(12) United States Patent
Hoge et al.

(10) Patent No.: US 10,328,423 B2
(45) Date of Patent: Jun. 25, 2019

(54) PERFLUOROALKYL GROUP-CONTAINING BISMUTH COMPOUNDS AS LEWIS ACID CATALYSTS

(71) Applicant: MERCK PATENT GMBH, Darmstadt (DE)

(72) Inventors: Berthold Theo Hoge, Bielefeld (DE); Sven Joerg-Ruediger August Solyntjes, Bielefeld (DE); Anne Julia Bader, Bielefeld (DE); Nikolai Ignatiev, Duisburg (DE)

(73) Assignee: MERCK PATENT GMBH, Darmstadt (DE)

( * ) Notice: Subject to any disclaimer, the term of this patent is extended or adjusted under 35 U.S.C. 154(b) by 0 days.

(21) Appl. No.: 15/762,869

(22) PCT Filed: Sep. 16, 2016

(86) PCT No.: PCT/EP2016/001557
§ 371 (c)(1),
(2) Date: Mar. 23, 2018

(87) PCT Pub. No.: WO2017/050425
PCT Pub. Date: Mar. 30, 2017

(65) Prior Publication Data
US 2018/0272325 A1 Sep. 27, 2018

(30) Foreign Application Priority Data
Sep. 23, 2015 (DE) .......... 10 2015 012 193

(51) Int. Cl.
*B01J 31/12* (2006.01)
*C07D 307/77* (2006.01)
*C07F 7/18* (2006.01)

(52) U.S. Cl.
CPC .......... *B01J 31/122* (2013.01); *C07D 307/77* (2013.01); *C07F 7/188* (2013.01); *B01J 2231/326* (2013.01); *B01J 2231/342* (2013.01); *B01J 2231/343* (2013.01)

(58) Field of Classification Search
CPC .................................................... B01J 31/122
USPC .......................................................... 549/237
See application file for complete search history.

(56) References Cited

FOREIGN PATENT DOCUMENTS

EP 1344772 A2 9/2003

OTHER PUBLICATIONS

International Search Report PCT/EP2016/001557 dated Jan. 2, 2017.
Gowravaram Sabitha et al: "BiCl 3-Catalyzed Diastereoselective Intramolecular [4+2] Cycloaddition Reactions Leading to Pyrazole Annulated New Sulfur Heterocycles", Synthetic Communications, vol. 33, No. 17, Sep. 1, 2003 (Sep. 1, 2003), Philadelphia, PA; US, pp. 3063-3070.
Dieter Naumann et al: "An alternative route for the synthesis of tris(trifluoromethyl)bismuth, Bi(CF3)3", Journal of Fluorine Chemistry, vol. 66, No. 1, Jan. 1, 1994 (Jan. 1, 1994), NL, pp. 79-80.
Kirij N V et al: "Synthesis and characterization of aryl(trifluoromethyl)bismuth compounds (R-C6H4)3-nBi(CF3)n [R=H, 4-CH3, 4-CF3, 3-F, 4-F; n=1 and 2] and the reactions of (C6H5)3-nnBi(CF3)n [n=0–3] with benzoylpyridinium chloride", Journal of Fluorine Chemistry, Elsevier, NL, vol. 69, No. 3, Dec. 1, 1994 (Dec. 1, 1994), pp. 219-223.
Dieter Naumann et al: "The preparations and properties of tris(perfluoroorgano)bismuth compounds Bi(Rf)3 (Rf=CF3, C2F5, n-C3F7, n-C4F9, n-C6F13, n-C8 F17, C6F5)", Journal of Organometallic Chemistry., vol. 334, No. 3, Nov. 1, 1987 (Nov. 1, 1987), CH, pp. 323-328.
Thierry Ollevier: "New trends in bismuth-catalyzed synthetic transformations", Organic & Biomolecular Chemistry, vol. 11, No. 17, Jan. 1, 2013 (Jan. 1, 2013), GB, pp. 2740, XP055327916, ISSN: 1477-0520.
Acid Catalysis in Modern Organic Synthesis, H. Yamamoto and K. Ishihara (Eds.), Wiley-VCH, Weinheim, 2008.
F.H.A. Kwie et al, Synthetic Communications, 40, 2010, 1082-1087.
S. Kobayashi et al, Chem. Eur. J., 12, 2006, 5954-5960.
R. Qiu et al, Adv. Synth. Catal, 352, 2010, 153-162.
T.C. Wabnitz et al, Chem. Eur. J. 10, 2004, 484-493.
W. Tyrra et al, Can. J. Chem., 1989, 67, 1949-1951.
Adonin et al, Z. Anorg. Allg. Chem., 2007, 633, 647-652.
S. Pasenok et al, J. Organomet. Chem., 1991, 417, C47-C49.
S. Faleschini et al, Journal of Organometallic Chemistry, 1972, 44, 317-323.
Barton et al, Tetrahedron, 1986, 42, 3111-3122.

*Primary Examiner* — Taofiq A Solola
(74) *Attorney, Agent, or Firm* — Millen White Zelano and Branigan, PC; Csaba Henter

(57) ABSTRACT

The invention relates to perfluoroalkyl group-containing bismuth compounds as Lewis acid catalysts, to specific compounds, and to the method for the production thereof.

17 Claims, No Drawings

PERFLUOROALKYL GROUP-CONTAINING BISMUTH COMPOUNDS AS LEWIS ACID CATALYSTS

The invention relates to bismuth compounds containing perfluoroalkyl groups as Lewis acid catalysts, to specific compounds, and to processes for the preparation thereof.

Catalysis using Lewis acids is a widespread method in organic synthesis and of outstanding importance for the industrial preparation of various substances. The numerous important industrial processes that are catalysed by Lewis acids include, for example, Friedel-Crafts alkylations and acylations of aromatic compounds, Gattermann-Koch reactions, Beckmann and Fries rearrangements, Mukaiyama aldol condensations [*Acid Catalysis in Modern Organic Synthesis*, H. Yamamoto and K. Ishihara (Eds.), WILEY-VCH, Weinheim, 2008].

G. N. Lewis defines an acid as a substance which is able to act as electron-pair acceptor. In accordance with this definition, Lewis acids are electron-deficient molecules or species. The Lewis-acidic catalysts usually used, such as $AlCl_3$, $TiCl_4$, $ZnCl_2$ and $BF_3$ diethyl etherate, are moisture-sensitive and generally cannot be recovered after completion of the reaction.

Further known Lewis acids are bismuth salts, such as $BiCl_3$, $BiBr_3$ and $Bi(OSO_2CF_3)_3$, as described in T. Ollevier, org. Biomol. Chem., 2013, 11, 2740-2755. When $BiCl_3$ is used as catalyst, however, a high concentration is necessary, generally 10 mol %, and the liberation of HCl can lead to corrosion of the reaction apparatus if, for example, steel vessels are used. The best-known bismuth catalyst is bismuth triflate. The disadvantage of this compound is the sensitivity to hydrolysis in the presence of water and its reactivity with alcohols and amines.

F. H. A. Kwie et al, Synthetic Communications, 40, 2010, 1082-1087 or T. C. Wabnitz et al, Chem. Eur. J. 10, 2004, 484-493, describe that any trifluoromethanesulfonic acid ($CF_3SO_3H$) liberated from the bismuth triflate could be responsible for the catalysis.

S. Kobayashi et al, Chem. Eur. J., 12, 2006, 5954-5960, propose that Bi(III) salts could be stabilised by the use of organic ligands, such as, for example, 2,2'-bipyridine derivatives.

R. Qiu et al, Adv. Synth. Catal, 352, 2010, 153 report on the use of bismuth perfluoroctanesulfonates as catalysts.

There therefore also continues to be a need for alternative Lewis acid catalysts in order that reactions catalysed by Lewis acids can be carried out optimally.

The object of the present invention is therefore to develop alternative Lewis acid catalysts which make it possible to carry out the reactions to be catalysed in good yield.

Surprisingly, it has been found that specific bismuth compounds which contain perfluoroalkyl groups are catalytically active and indeed are more catalytically active than $BiCl_3$.

W. Tyrra et al, Can. J. Chem., 1989, 67, 1949-1951, and D. Naumann et al, J. Organomet. Chem., 1987, 334, 323-328, disclose the bismuth compounds $Bi(CF_3)_3$, $Bi(CF_3)_2Cl$, $Bi(CF_3)Cl_2$, $Bi(CF_3)_2F$, $Bi(C_2F_5)_3$, $Bi(n-C_3F_7)_3$, $Bi(n-C_4F_9)_3$, $Bi(n-C_6F_{13})_3$ and $Bi(n-C_8F_{17})_3$. An application of these compounds was not described.

S. Pasenok et al, J. Organomet. Chem., 1991, 417, C47-C49, disclose the compounds diphenyl(trifluoromethyl)bismuth and phenylbis(trifluoromethyl)-bismuth. The compounds are prepared by reaction of $Cd(CF_3)_2 \cdot 2\ CH_3CN$ with phenylbismuth halides. The compounds are described as air-sensitive.

N. V. Kirij et al, J. Fluorine Chem., 1994, 69, 219-223, likewise describe aryl(trifluoromethyl)bismuth compounds, in which the aryl group was varied, and the reaction thereof with benzoylpyridinium chloride.

The invention therefore relates firstly to the use of at least one compound of the formula (I)

$$(C_mF_{2m+1})_nBiX_{3-n} \qquad (I),$$

where m in each case, independently of one another, denotes 2, 3 or 4;

n denotes 1, 2 or 3 and

X denotes F, Cl, Br or $OSO_2CF_3$, as Lewis acid catalyst.

In a preferred embodiment of the invention, the perfluoroalkyl group $(C_mF_{2m+1})$ is preferably the same on each occurrence.

The invention therefore furthermore relates to the use of at least one compound of the formula (I), as described above, where the perfluoroalkyl group $(C_mF_{2m+1})$ is the same on each occurrence.

The perfluoroalkyl group $(C_mF_{2m+1})$, where m denotes 2, 3 or 4, is preferably pentafluoroethyl, n-heptafluoropropyl, iso-heptafluoropropyl, n-nonafluorobutyl, sec-nonafluorobutyl or tert-nonafluorobutyl. The perfluoroalkyl group $(C_mF_{2m+1})$ particularly preferably stands for pentafluoroethyl or n-nonafluorobutyl.

The invention therefore furthermore relates to the use of at least one compound of the formula (I), as described above and preferably, where the perfluoroalkyl group $(C_mF_{2m+1})$ denotes pentafluoroethyl or n-nonafluorobutyl.

In a further preferred embodiment of the invention, compounds of the formula (I) are used in which n is 1 or 2. Preferred compounds of the formula (I) in the use as Lewis acid catalysts are compounds in which X denotes Cl.

The invention therefore furthermore relates to the use of at least one compound of the formula (I), as described above and preferably, where X denotes Cl.

The invention furthermore also relates to the compounds of the formula (I)

$$(C_mF_{2m+1})_nBiX_{3-n} \qquad (I),$$

where m in each case, independently of one another, denotes 2, 3 or 4;

n denotes 1 or 2 and

X denotes F, Cl, Br or $OSO_2CF_3$.

Preferred compounds of the formula (I) in which n denotes 1 or 2 are compounds in which X denotes Cl or F.

Particularly preferred compounds of the formula (I) in which n denotes 1 or 2 are compounds in which X denotes Cl.

The invention therefore furthermore relates to the compounds of the formula (I), as described above, characterised in that X denotes Cl.

Particularly preferred compounds are compounds of the formula (I) in which X denotes Cl and m denotes 2 or 4. Very particularly preferred compounds are compounds of the formula (I) in which X denotes Cl and m denotes 2

Very particularly preferred Lewis acid catalysts are the compounds $Bi(C_2F_5)_3$, $Bi(C_2F_5)Cl_2$ and $Bi(C_2F_5)_2Cl$.

The compounds of the formula (I) in which n denotes 3 can be prepared on the basis of known synthetic methods, for example using cadmium complexes, as described in D. Naumann et al, J. Organomet. Chem., 1987, 334, 323-328, or zinc complexes, as described in D. Naumann et al, J. Fluorine Chem. 1994, 66 (1), 79-80.

However, cadmium complexes are disadvantageous starting materials from an economic point of view.

The invention therefore furthermore relates to a process for the preparation of compounds of the formula (I), as described above, where n denotes 3, characterised in that a compound of the formula (II)

$$(C_mF_{2m+1})Li \qquad (II),$$

where m denotes 2, 3 or 4, is reacted with bismuth trichloride, bismuth tribromide or bismuth tristriflate, preferably with bismuth trichloride, where the conditions of the reactions are selected in such a way that both the water content and also the oxygen content are a maximum of 100 ppm.

The reaction, as described above or described below, takes place in an inert-gas atmosphere whose oxygen content is a maximum of 100 ppm. It is particularly preferred if the oxygen content is less than 100 ppm, very particularly preferably a maximum of 50 ppm.

The water content of the reagents and of the inert-gas atmosphere is a maximum of 100 ppm. It is particularly preferred if the water content of the reagents and of the atmosphere is less than 100 bpm, very particularly preferably 5 to 50 ppm.

The conditions with respect to the water content and the oxygen content do not apply to the work-up after successful reaction of compounds of the formula (II) or the compounds of the formula (IIIa) and (IIIb), as described below.

As an alternative to compounds of the formula (II), it is possible to use Grignard reagents, which conform, for example, to the formula (IIA), $$(C_mF_{2m+1})MgY \qquad (IIA),$$

where m denotes 2, 3 or 4 and Y denotes I or Br. The reaction conditions mentioned for the reaction with compounds of the formula (II), that both the water content and also the oxygen content should be a maximum of 100 ppm, also apply correspondingly to the reaction of the compounds of the formula (IIA).

The compounds of the formula (IIA) can be prepared on the basis of known synthetic methods.

Bismuth trichloride, bismuth tribromide and bismuth tristriflate are commercially available.

The compounds of the formula (II) can be prepared on the basis of known synthetic methods.

A variant of the synthesis of the compounds of the formula (II) is the reaction of the corresponding monohydridoperfluoroalkane ($HC_mF_{2m+1}$) with a 2M solution of n-butyllithium in pentane in dry diethyl ether, as described in the example part.

Alternatively, a compound of the formula (II) can be prepared from perfluoroalkyl iodides, as described in N. Yu. Adonin et al, Z. Anorg. Allg. Chem., 2007, 633, 647-652.

For the further reaction of the compound of the formula (II), as described above, with bismuth trichloride, bismuth tribromide or bismuth tristriflate, the reaction is preferably carried out without further purification.

Alternatively, the compounds of the formula (II) can be prepared by reaction of a tris(perfluoroalkyl)phosphine ($P(C_mF_{2m+1})_3$) with a 1.6M solution of n-butyllithium in hexane, as described in the example part. For the further reaction of the compound of the formula (II), as described above, with bismuth trichloride, bismuth tribromide or bismuth triflate, the reaction is preferably carried out without further purification.

The reaction with bismuth trichloride is carried out directly after the in situ preparation of the compound of the formula (II), as described above, in the solvent or solvent mixture present.

The starting materials are preferably mixed at low temperature, for example at temperatures between −100° C. and −65° C. The mixture is then preferably warmed to a temperature between −10° C. and 5° C., preferably to 0° C. The reaction mixture is then filtered under an inert-gas atmosphere.

This is preferably followed by a suitable purification method. For example washing of the residue with a suitable solvent and subsequent sublimation.

The invention furthermore relates to a process for the preparation of compounds of the formula (I) where n denotes 1 or 2, characterised in that a compound of the formula (II)

$$(C_mF_{2m+1})Li \qquad (II),$$

where m in each case, independently of one another, denotes 2, 3 or 4, is in a first reaction reacted with dichloroarylbismuthane or chloro(diaryl)bismuthane, where aryl in the corresponding bismuthane denotes an aryl group having 6 to 10 C atoms, which may be substituted or unsubstituted, and the intermediates of the formula (IIIa) or (IIIb)

$$ArBi(C_mF_{2m+1})_2 (IIIa) \text{ or } Ar_2Bi(C_mF_{2m+1}) \text{ (IIIb)},$$

are subsequently reacted with hydrogen chloride, hydrogen bromide, anhydrous HF or trifluoromethanesulfonic acid to give compounds of the formula (I), where Ar in each case, independently of one another, denotes an aryl group having 6 to 10 C atoms, which may be substituted or unsubstituted, and where the conditions of the reactions with the compound of the formula (II) are selected in such a way that both the water content and also the oxygen content are a maximum of 100 ppm.

As an alternative to compounds of the formula (II), it is also possible to carry out this reaction using Grignard reagents, which conform, for example, to the formula (IIA), $$(C_mF_{2m+1})MgY \qquad (IIA),$$

where m denotes 2, 3 or 4 and Y denotes I or Br. The reaction conditions mentioned for the reaction with compounds of the formula (II), that both the water content and also the oxygen content should be a maximum of 100 ppm, also apply correspondingly to the reaction of the compounds of the formula (IIA).

The invention furthermore likewise relates to the compounds of the formula (IIIa) and (IIIb)

$$ArBi(C_mF_{2m+1})_2 \qquad (IIIa),$$

$$Ar_2Bi(C_mF_{2m+1}) \qquad (IIIb),$$

where m in each case, independently of one another, denotes 2, 3 or 4 and Ar in each case, independently of one another, denotes an aryl group having 6 to 10 C atoms, which may be substituted.

An aryl group having 6 to 10 C atoms denotes phenyl or naphthyl, which may be mono- or polysubstituted by alkyl, fluorinated alkyl, Oalkyl or N(alkyl)$_2$.

"Alkyl" denotes a linear or branched alkyl group having 1 to 10 C atoms. "Fluorinated alkyl" is a linear or branched fluorinated alkyl group having 1 to 10 C atoms, where at least one H atom of a linear or branched alkyl group having 1 to 10 C atoms has been replaced by an F atom. It is also possible for all H atoms to have been replaced by F atoms.

The aryl group is preferably phenyl which is unsubstituted or monosubstituted by alkyl, fluorinated alkyl, Oalkyl or N(alkyl)$_2$. Ar is particularly preferably an unsubstituted phenyl group or a phenyl group which is monosubstituted by alkyl. Ar is very particularly preferably an unsubstituted phenyl group.

A straight-chain or branched alkyl group having 1 to 10 C atoms is, for example, methyl, ethyl, isopropyl, propyl, butyl, sec-butyl or tert-butyl, pentyl, 1-, 2- or 3-methylbutyl, 1,1-, 1,2- or 2,2-dimethylpropyl, 1-ethyl-propyl, n-hexyl, n-heptyl, n-octyl, n-nonyl or n-decyl.

"Fluorinated alkyl" is preferably a straight-chain or branched fluorinated alkyl group having 1 to 4 C atoms. "Fluorinated alkyl" is particularly preferably trifluoromethyl, pentafluoroethyl, heptafluoroisopropyl, heptafluoropropyl and nonafluorobutyl.

The compound of the formula (IIIa) is particularly preferably bis(pentafluoroethyl)phenylbismuthane.

The compound of the formula (IIIb) is particularly preferably pentafluoroethyldiphenylbismuthane.

The compounds of the formula (IIIa) and (IIIb) are likewise suitable as Lewis acid catalysts.

The invention therefore furthermore relates to the use of at least one compound of the formula (IIIa) or (IIIb), as described above or preferably described, as Lewis acid catalyst.

The invention therefore furthermore likewise relates to a process for the preparation of compounds of the formula (IIIa) or (IIIb), characterised in that a compound of the formula (II)

$(C_mF_{2m+1})Li$      (II), where m in each case, independently of one another, denotes 2, 3 or 4, is reacted with dichloroarylbismuthane or chloro(diaryl)bismuthane, where aryl in the corresponding bismuthane denotes an aryl group having 6 to 10 C atoms, which may be substituted or unsubstituted.

The compounds of the formula (II) can likewise be prepared in situ, as described above.

Dichlorophenylbismuthane is commercially available. The synthesis of dichlorophenylbismuthane and diphenylchlorobismuthane is described, for example, in S. Faleschini et al, *Journal of Organometallic Chemistry*, 1972, 44, 317-323, or in D. H. R. Barton et al, *Tetrahedron*, 1986, 42, 3111-3122. The compounds dichloroarylbismuthane and diarylchlorobismuthane can be prepared analogously to these processes.

The reaction with dichloroarylbismuthane or chloro(diaryl)bismuthane, preferably the reaction of dichloroarylbismuthane, is carried out directly after the in situ preparation of the compound of the formula (II), as described above, in the solvent or solvent mixture present to give the compounds of the formula (IIIa) or (IIIb).

The starting materials are preferably mixed at low temperature, for example at temperatures between −100° C. and −65° C. The mixture is then preferably warmed to a temperature between −10° C. and 5° C., preferably to 0° C. The reaction mixture is then filtered under an inert-gas atmosphere.

This is preferably followed by a suitable purification method for the isolation of the compounds of the formula (IIIa) or (IIIb). For example washing of the residue with a suitable solvent and subsequent sublimation or crystallisation.

For the reaction with hydrogen chloride, hydrogen bromide, anhydrous HF or trifluoromethanesulfonic acid, the isolated compound of the formula (IIIa) or of the formula (IIIb) is initially introduced and preferably degassed. Hydrogen chloride, hydrogen bromide, anhydrous HF or trifluoromethanesulfonic acid is then condensed in, and the reaction mixture is stirred, preferably at temperatures of 0° C. to 70° C., particularly preferably at a bath temperature of 10° C. to 60° C. Excess hydrogen chloride or hydrogen bromide or excess HF or trifluoromethanesulfonic acid is removed by condensation, and the residue is preferably sublimed for purification.

Compounds of the formula (I), as described above, in which X denotes F or OSO$_2$CF$_3$ can alternatively be prepared from corresponding compounds of the formula (I) in which X denotes Cl by reaction with AgF or AgOSO$_2$CF$_3$. The reaction is preferably carried out in an organic solvent or in a mixture of organic solvents. A mixture of dichloromethane and acetonitrile (1:1) is particularly preferably employed. The reaction temperature is preferably room temperature. It is furthermore preferred to carry out the reaction under inert-gas conditions and with exclusion of light.

The invention furthermore relates to a Lewis acid catalyst of the formula (I) or of the formulae (IIIa) and (IIIb), as described above or preferably described, for use in a Lewis acid-catalysed reaction.

In a preferred embodiment of the invention, the Lewis acid-catalysed reaction is selected from a condensation reaction, alcoholysis, aldol reaction, Mukaiyama aldol reaction, Gattermann-Koch reaction, Beckmann- and Fries rearrangement, Friedel-Crafts acylation, Friedel-Crafts alkylation, Mannich reaction, Diels-Alder reaction, aza Diels-Alder reaction, Baylis-Hillman reaction, Reformatsky reaction, Claisen rearrangement, Prins cyclisation reaction, allylation of carbonayl compounds, cyanation of aldehydes and ketones, cyanosilylation of aldehydes and ketones, 1,3-dipolar cycloaddition or Michael reaction.

The compounds of the formula (I) are preferably employed in a sub-stoichiometric amount of catalyst of 0.01 to 10 mol %, based on the starting material. The compounds of the formula (I), as described above or as preferably described, are particularly preferably employed in an amount of 1 to 5 mol %. The person skilled in the art in the area of catalysis is able to select the optimum amount of catalyst for the corresponding reaction to be catalysed. The results in the example part confirm that (C$_2$F$_5$)BiCl$_2$ and (C$_2$F$_5$)$_2$BiCl are significantly more active catalysts in the Diels-Alder reaction, compared with BiCl$_3$.

Owing to the specific solution properties of the compounds of the formula (I), as described above or as preferably described, the choice of solvent for the Lewis acid-catalysed reaction is crucial.

Suitable protic solvents on use of the Lewis acid catalysts according to the invention are ethanol or methanol.

Suitable aprotic solvents on use of the Lewis acid catalysts according to the invention are acetonitrile, propionitrile, benzonitrile, nitromethane, diethyl ether, methyl tert-butyl ether 1,4-dioxane, tetrahydrofuran, 2-methyltetrahydrofuran, dichloromethane, 1,2-dichloroethane, monoglyme, diglyme, triglyme, hexane, heptane, petroleum ether, benzene or toluene.

The class of the ionic liquids are also suitable as solvents on use of the Lewis acid catalysts according to the invention.

An ionic liquid is taken to mean salts which generally consist of an organic cation and an inorganic anion. They do not contain any neutral molecules and usually have melting points below 373 K [Wasserscheid P, Keim W, *Angew. Chem.* 112, 2000, 3926]. Due to their salt character, ionic liquids have unique substance properties, such as, for example, a low vapour pressure, a liquid state over a broad temperature range, are non-flammable, exhibit high electrical conductivity and high electrochemical and thermal stability.

Suitable ionic liquids as solvents on use of the Lewis acid catalysts according to the invention are ionic liquids which have an organic cation and whose anion is selected from the group $[R_1SO_3]^-$, $[R_2COO]^-$, $[R_2SO_3]^-$, $[R_1OSO_3]^-$, $[BF_4]^-$, $[HSO_4]^{1-}$, $[(R_1)_2P(O)O]^-$, $[(R_2)_2P(O)O]^-$, $[R_2P(O)O_2]^{2-}$, $[(FSO_2)_2N]^-$, $[(R_2SO_2)_2N]^-$, $[(R_2SO_2)_3C]^-$, $[(FSO_2)_3C]^-$, $[P(R_2)_yF_{6-y}]^-$, $[BF_x(R_2)_{4-x}]^-$, $[BF_x(CN)_{4-x}]^-$, $[B(R_1)_a(CN)_{4-a}]^-$, $[B(R_2)F_2(CN)]^-$ or $[B(R_2)F(CN)_2]^-$, where $R_1$ in each case, independently of one another, denotes a linear or branched alkyl group having 1 to 12 C atoms, $R_2$ in each case, independently of one another, denotes a partially fluorinated or perfluorinated linear or branched alkyl group having 1 to 12 C atoms or pentafluorophenyl, x denotes the integer 0, 1, 2 or 3, y denotes the integer 0, 1, 2, 3 or 4 and a denotes the integer 1 or 2.

A perfluorinated linear or branched alkyl group having 1 to 4 C atoms is, for example, trifluoromethyl, pentafluoroethyl, n-heptafluoropropyl, iso-heptafluoropropyl, n-nonafluorobutyl, sec-nonafluorobutyl or tert-nonafluorobutyl. $R_2$ analogously defines a linear or branched perfluorinated alkyl group having 1 to 12 C atoms, including the above-mentioned perfluoroalkyl groups and, for example, perfluorinated n-hexyl, perfluorinated n-heptyl, perfluorinated n-octyl, perfluorinated ethylhexyl, perfluorinated n-nonyl, perfluorinated n-decyl, perfluorinated n-undecyl or perfluorinated n-dodecyl.

$R_2$ is preferably trifluoromethyl, pentafluoroethyl or nonafluorobutyl, very particularly preferably trifluoromethyl or pentafluoroethyl.

The variable y is preferably 1, 2 or 3, particularly preferably 3.

Preferred solvents are ionic liquids with the anions $[P(R_2)_yF_{6-y}]^-$ and $[R_2SO_3]^-$, where $R_2$ and y have a meaning indicated above or indicated as preferred.

Particularly preferred solvents are ionic liquids with the anions $[P(C_2F_5)_3F_3]^-$ and $[CF_3SO_3]^-$.

The organic cations are generally unrestricted and are preferably selected from imidazolium cations, pyridinium cations or pyrrolidinium cations, which may be appropriately substituted, as known from the prior art.

The ionic liquid 1-ethyl-3-methylimidazolium tris(pentafluoroethyl)trifluoro-phosphate {[EMIM][FAP]} is very particularly preferably selected as solvent.

The following examples of Lewis acid-catalysed reactions show that the use of the compounds of the formula (I), as described above or described as preferred, can likewise achieve very good yields in direct comparison with $BiCl_3$, but where the amount of catalyst is significantly reduced in the case of the Lewis acid catalysts according to the invention.

The suitability of the compounds of the formula (I) as Lewis acid catalysts has been confirmed with reference to a Diels-Alder reaction and a cyanosilylation of an aldehyde. These reaction types are representative of Lewis acid-catalysed reactions.

Even without further comments, it is assumed that a person skilled in the art will be able to utilise the following descriptions in the broadest scope. The preferred embodiments and examples should therefore merely be regarded as as descriptive disclosure which is absolutely not limiting in any way.

EXAMPLES

Example 1

Synthesis of tris(pentafluoroethyl)bismuthane, $Bi(C_2F_5)_3$

A)

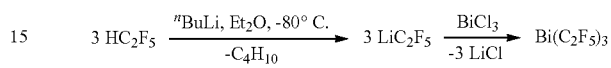

50 ml (100 mmol) of a 2 M solution of n-buthyllithium in pentane in 200 ml of dry diethyl ether are initially introduced into a 500 ml Schlenk flask and degassed at −90° C. in a counterstream of nitrogen. 12.3 g (102.5 mmol) of pentafluoroethane are condensed in at −80° C., and the mixture is stirred at the same temperature for 30 minutes. 6.31 g (20.0 mmol) of bismuth trichloride, $BiCl_3$, are added in a counterstream of nitrogen. The reaction mixture is stirred at −80° C. for 60 minutes and then warmed to 0° C. over the course of 4 hours. The reaction mixture is filtered under an inert-gas atmosphere, and the residue is washed twice with 20 ml of dry n-pentane each time. The reaction mixture is evaporated in a static vacuum (70 mbar). The remaining solvent is removed in a sublimation apparatus in a high vacuum, and the reaction product is sublimed on a cold finger cooled with dry ice (−50° C. to −30° C.). After warming to room temperature, 7.16 g of tris(pentafluoroethyl)bismuthane, $Bi(C_2F_5)_3$, are obtained as a colourless liquid. Yield (based on bismuth trichloride): 63% (12.6 mmol).

Melting point: ~−10° C.

The NMR data correspond to the values known from the literature [D. Naumann, W. Tyrra, *J. Organomet. Chem.* 1987, vol. 334, pp. 323-328].

TABLE

NMR data of tris(pentafluoroethyl)bismuthane, $Bi(C_2F_5)_3$, in $CH_3CN$

| Nucleus | δ [ppm] | Splitting | J [Hz] | Assignment |
|---|---|---|---|---|
| $^{19}F$ | −82.1 | s | — | $CF_3CF_2$ |
|  | −100.1 | s | — | $CF_3CF_2$ |
| $^{13}C, ^{19}F$-DEPT 45nd | 122.6 | qt | $^1J_{CF} = 285$ | $CF_3CF_2$ |
|  | 160.9 | m |  | $CF_3CF_2$ |

TABLE

Mass spectrometry data of tris(pentafluoroethyl)bismuthane, $Bi(C_2F_5)_3$, EI-TOF (gas inlet), positive, 70 eV.

| m/z | Rel. intensity (%) | Fragment |
|---|---|---|
| 466.9 | 50 | $[BiF(C_2F_5)_2]^+$ |
| 346.9 | 100 | $[BiF[(C_2F_5)]^+$ |

B)

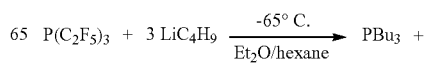

-continued

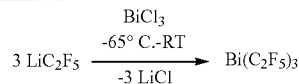

A 1.6 M solution of n-butyllithium in hexane (0.80 ml, 1.28 mmol) is added to a solution of 171 mg (0.44 mmol) of P(C$_2$F$_5$)$_3$ in Et$_2$O (10 ml) at −65° C., and the mixture is stirred for 10 minutes. 0.15 g (0.48 mmol) of BiCl$_3$ are added at the same temperature, and the reaction mixture is slowly warmed to room temperature. The solution is investigated by NMR spectroscopy. The NMR data confirm the formation of Bi(C$_2$F$_5$)$_3$.

Example 2

Preparation of bis(pentafluoroethyl)phenylbismuthane, PhBi(C$_2$F$_5$)$_2$

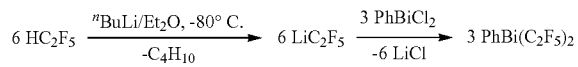

22 ml (44.0 mmol) of a 2 M solution of n-buthyllithium in pentane in 100 ml of Et$_2$O are initially introduced in a 250 ml Schlenk flask and degassed at −80° C. 5.40 g (45 mmol) of pentafluoroethane are condensed in at −80° C., and the mixture is stirred at the same temperature for 25 minutes. 3.87 g (10.8 mmol) of dichlorophenylbismuthane are added, and the mixture is stirred in a cold bath at −80° C. for 3.5 hours. The suspension is filtered in an inert-gas atmosphere and evaporated in a static high vacuum. The remaining solvent is removed in a sublimation apparatus in a high vacuum and at an oil-bath temperature of 80° C., and the reaction product is sublimed on a cold finger cooled with dry ice (−35° C.). Warming to room temperature gives 4.22 g of bis(pentafluoroethyl)phenylbismuthane, PhBi(C$_2$F$_5$)$_2$, as a colourless liquid.

Yield (based on dichlorophenylbismuthane): 8.1 mmol, 75%.

Melting point: −15° C.

The product is characterised by means of NMR and IR spectroscopy and by mass spectrometry.

TABLE

NMR data of bis(pentafluoroethyl)phenylbismuthane, PhBi(C$_2$F$_5$)$_2$, in CD$_3$CN.

| Nucleus | δ [ppm] | Splitting | J [Hz] | Assignment |
|---|---|---|---|---|
| $^1$H | 8.2 | d | $^3J_{HH}$ = 7 | ortho H |
|  | 7.7 | t | $^3J_{HH}$ = 7 | meta H |
|  | 7.5 | t | $^3J_{HH}$ = 7 | para H |
| $^{19}$F | −82.4 | m | — | (CF$_3$CF$_2$)$_2$Bi Ph |
|  | −105.8 | s | — | (CF$_3$CF$_2$)$_2$Bi Ph |
| $^{13}$C-CPD; | 170.4 | s |  | quart. C |
| $^1$H,$^{13}$C-HMBC | 138.7 | s |  | ortho C |
|  | 132.0 | s |  | meta C |
|  | 130.1 | s |  | para C |
| $^{13}$C,$^{19}$F-DEPT45; | 122.3 | qm | $^1J_{CF}$ = 283 | CF$_3$CF$_2$ |
| $^{13}$C,$^{19}$F-HMBC | 148.3 | tm |  | CF$_3$CF$_2$ |

TABLE

Mass spectrometry data of bis(pentafluoroethyl)phenyl-bismuthane, PhBi(C$_2$F$_5$)$_2$, EI-TOF (gas inlet), positive, 70 eV.

| m/z | rel. intensity (%) | Fragment |
|---|---|---|
| 405.0 | 56 | [(C2F5)BiPH]+ |
| 286.1 | 62 | [PhBi]+ |
| 209.0 | 91 | Bi+ · |

IR: ṽ = 3065 (w), 2965 (w), 1303 (m), 1182 (s), 1070 (s), 896 (s), 726 (s), 691 (m), 600 (w) 533 (w), 442 (w)

Example 3

Preparation of bis(pentafluoroethyl)chlorobismuthane, (C$_2$F$_5$)$_2$BiCl

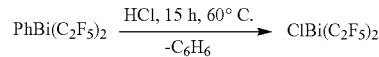

4.02 g (7.7 mmol) of bis(pentafluoroethyl)phenylbismuthane, PhBi(C$_2$F$_5$)$_2$, are initially introduced in a 800 ml Young's tap ampoule and degassed. 1.09 g (30.0 mmol) of hydrogen chloride are condensed in, and the mixture is stirred at an oil-bath temperature of 60° C. for 2.5 h. Excess hydrogen chloride is removed by condensation, and the residue is sublimed at 90° C. in a high vacuum, giving bis(pentafluoroethyl)chlorobismuthane, (C$_2$F$_5$)$_2$BiCl, as a yellow solid. Yield (based on bis(pentafluoroethyl)phenylbismuthane): 3.45 g (7.2 mmol, 92%). Melting point: 75-76° C. The product is characterised by means of NMR and IR spectroscopy and by mass spectrometry.

TABLE

NMR data of bis(pentafluoroethyl)chlorobismuthane, (C$_2$F$_5$)$_2$BiCl, in CH$_3$CN.

| Nucleus | δ [ppm] | Splitting | J [Hz] | Assignment |
|---|---|---|---|---|
| $^{19}$F | −80.6 | s | — | CF$_3$CF$_2$ |
|  | −103.0 | s | — | CF$_3$CF$_2$ |

TABLE

NMR data of bis(pentafluoroethyl)chlorobismuthane, (C$_2$F$_5$)$_2$BiCl, in CH$_2$Cl$_2$.

| Nucleus | δ [ppm] | Splitting | J [Hz] | Assignment |
|---|---|---|---|---|
| $^{19}$F | −80.8 | s | — | CF$_3$CF$_2$ |
|  | −101.7 | AA'BB' | — | CF$_3$CF$_2$ |

TABLE

Mass spectrometry data of bis(pentafluoroethyl)-chlorobismuthane, (C$_2$F$_5$)$_2$BiCl, EI-TOF (gas inlet), positive, 70 eV.

| m/z | rel. intensity (%) | Fragment |
|---|---|---|
| 467.1 | 20 | [BiF(C$_2$F$_5$)$_2$]$^+$ |
| 447.1 | 33 | [Bi(C$_2$F$_5$)$_2$]$^+$ |
| 347.1 | 48 | [BiF[(C$_2$F$_5$)]$^+$ |
| 328.1 | 6 | [Bi(C$_2$F$_5$)]$^+$ |

TABLE-continued

Mass spectrometry data of bis(pentafluoroethyl)-
chlorobismuthane, $(C_2F_5)_2BiCl$, EI-TOF (gas inlet), positive, 70 eV.

| m/z | rel. intensity (%) | Fragment |
|---|---|---|
| 247.1 | 10 | $[BiF_2]^+$ |
| 209.0 | 59 | $Bi^+$ · |

IR: $\tilde{v}$ = 1301 (m), 1190 (s), 1129 (m), 1082 (s), 895 (s), 730 (m), 600 (m), 534 (w).

Example 4

Preparation of pentafluoroethyldiphenylbismuthane, $Ph_2BiC_2F_5$

A)

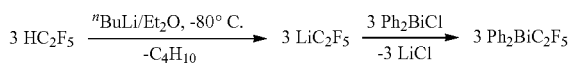

20 ml (40 mmol, 2 M in n-pentane) of n-BuLi in 150 ml of diethyl ether are initially introduced into a 500 ml Schlenk flask and degassed at −80° C. 5.4 g (45 mmol) of pentafluoroethane are condensed in, and the mixture is stirred at the same temperature for 10 min. 7.97 g (20 mmol) of chloro(diphenyl)bismuthane are added, the mixture is stirred at −60° C. for 4 h and subsequently warmed to room temperature. All volatile constituents are removed in a high vacuum, the residue obtained is taken up in n-pentane, filtered in an inert-gas atmosphere and washed with n-pentane. Removal of the solvent gives pentafluoroethyl(diphenyl)bismuthane, $Ph_2BiC_2F_5$, in the form of colourless crystals, which change colour to yellow-brown after a short time. Yield (based on chloro(diphenyl)bismuthane): 6.20 g (12.9 mmol, 65%).

IR: $\tilde{v}$; =3052 (w), 2957 (w), 1303 (m), 1568 (w), 1475 (w), 1428 (w), 1308 (m), 1262 (w), 1176 (s), 1075 (s), 903 (m), 800 (w), 724 (s), 692 (s), 596 (m) 533 (w), 442 (m)

TABLE

NMR data of pentafluoroethyldiphenylbismuthane in $CD_2Cl_2$.

| Nucleus | δ [ppm] | Splitting | J [Hz] | Assignment |
|---|---|---|---|---|
| $^1H$ | 7.9 | d | $^3J_{HH}$ = 7.2 | ortho H |
|  | 7.6 | t | $^3J_{HH}$ = 7.4 | meta H |
|  | 7.4 | t | $^3J_{HH}$ = 7.4 | para H |
| $^{19}F$ | −81.6 | s | — | $CF_3CF_2$ |
|  | −105.6 | AA'BB' | — | $CF_3CF_2$ |
| $^{13}C$-CPD | 160.5 | s |  | quart. C |
| $^1H,^{13}C$-HMBC | 137.8 | s |  | ortho C |
|  | 131.1 | s |  | meta C |
|  | 128.9 | s |  | para C |
| $^{13}C,^{19}F$-DEPT45; | 201.5 | s |  | $CF_3CF_2$ |
| $^{13}C,^{19}F$-HMBC | 129.4 | s |  | $CF_3CF_2$ |

B)

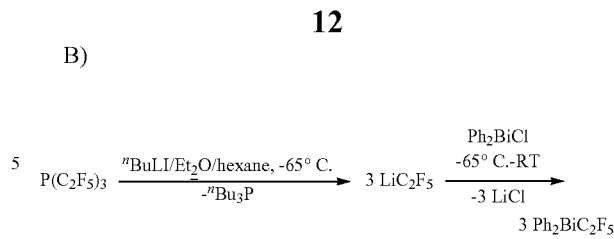

80 ml of diethyl ether are initially introduced into a 250 ml Schlenk flask and degassed at −196° C. 2.95 g (7.6 mmol) of tris(pentafluoroethyl)phosphine, $(C_2F_5)_3P$, are condensed in and brought to −65° C. 9.43 g (22.2 mmol; 13.9 ml) of a 1.6 M solution of n-BuLi in hexane are added to this mixture, which is then stirred at the same temperature for 15 min. 8.75 g (22.0 mmol) of chloro(diphenyl)bismuthane are added to the reaction mixture, which is then warmed to 0° C. for 3 h with stirring. The suspension obtained is filtered under an inert-gas atmosphere, the residue is washed with a little diethyl ether, and all volatile constituents of the filtrate are removed in a high vacuum. The residue obtained is taken up in 100 ml of n-pentane. The solution is evaporated until the first crystals form, and the product is crystallised out by cooling to −28° C. The crystals are washed with a little n-pentane and dried in a high vacuum, giving pentafluoroethyl-(diphenyl)bismuthane, $Ph_2BiC_2F_5$, in the form of colourless, hydrolysis-sensitive crystals. Yield (based on chloro(diphenyl)bismuthane): 8.57 g (17.8 mmol, 81%).

The product is characterised by means of NMR and IR spectroscopy. The NMR and IR data correspond to the values given in Example 4A).

Example 5

Preparation of pentafluoroethyldichlorobismuthane, $(C_2F_5)BiCl_2$

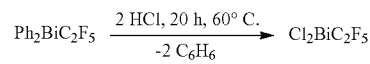

6.20 g (12.9 mmol) of diphenyl(pentafluoroethyl)bismuthane, $Ph_2BiC_2F_5$, are taken up in 25 ml of diethyl ether and transferred into an 800 ml Young's tap ampoule. The solvent is removed in a high vacuum, and 1.46 g (40 mmol) of hydrogen chloride are condensed in. The reaction mixture is stirred at an oil-bath temperature of 60° C. for 20 h. All volatile constituents are removed by condensation, the residue is taken up in dichloromethane and transferred into a 100 ml Schlenk flask. Sublimation in a high vacuum at an oil-bath temperature of 90° C. and a cold-finger temperature of −78° C. gives pentafluoroethyldichlorobismuthane, $C_2F_5BiCl_2$, as a yellow solid.

Yield (based on pentafluoroethyl(diphenyl)bismuthane): 4.67 g (11.7 mmol, 91%).

Melting point: 104° C.

The product is characterised by means of NMR, and IR spectrometry.

TABLE

NMR data of pentafluoroethyldichlorobismuthane, $C_2F_5BiCl_2$, in $CH_3CN$.

| Nucleus | δ [ppm] | Splitting | J [Hz] | Assignment |
|---|---|---|---|---|
| $^{19}F$ | −79.5 | s | $^1J_{CF} = 283$ | $CF_3CF_2$ |
|  |  |  | $^2J_{CF} = 44$ |  |
|  | −105.2 | s | $^1J_{CF} = 333$ | $CF_3CF_2$ |
| $^{19}F,^{13}C$-HMBC | 129.42 |  | $^1J_{CF} = 283$ | $CF_3CF_2$ |
|  |  |  | $^2J_{CF} = 44$ |  |
|  | 201.45 |  | $^1J_{CF} = 333$ | $CF_3CF_2$ |
|  |  |  | $^2J_{CF} = 27$ |  |

IR: ṽ = 1301 (m), 1267 (w), 1103 (s), 1073 (s), 897 (s), 729 (s), 603 (m), 584 (w), 531 (w).

Example 6

Preparation of bis(pentafluoroethyl)fluorobismuthane

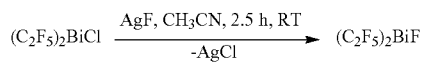

366 mg (2.885 mmol) of silver fluoride are added to a solution of $(C_2F_5)_2BiCl$ (1.38 g, 2.86 mmol) in a mixture of dichloromethane (10 ml) and acetonitrile (10 ml) in a counterstream of nitrogen. The reaction mixture is stirred at room temperature with exclusion of light for 2.5 h. The solid which precipitates out is filtered off under an inert-gas atmosphere, and the filtrate is evaporated in a high vacuum. Drying in a high vacuum gives $(C_2F_5)_2BiF$ as a colourless, slightly crystalline solid. Yield is 1.13 g (2.42 mmol, 85%, based on $(C_2F_5)_2BiCl$).

Decomposition point: >200° C.

TABLE

NMR data of $(C_2F_5)_2BiF$, in $CD_3CN$.

| Nucleus | δ [ppm] | Splitting | J [Hz] | Assignment |
|---|---|---|---|---|
| $^{19}F$ | −81.8 | s | $^1JCF = 282$ | CF3CF2 |
|  | −108.4 | s | — | CF3CF2 |
|  | −171.9 | s |  | BiF |
| $^{13}C,^{19}F$-DEPT45; | 125.7 | s | $^1JCF = 282$ | CF3CF2 |
| $^{13}C,^{19}F$-HMBC | 175.9 | — |  | CF3CF2 |

IR (solid): ṽ = 429 (vw), 535 (vw), 588 (vw), 602 (w), 732 (m), 899 (s), 1079 (s), 1186 (s), 1303 (m), 1648 (vw) cm$^{-1}$.

Example 7

Bismuth(III)-Catalysed Diels-Alder Reaction

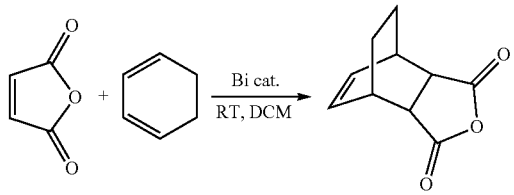

The Diels-Alder reaction of maleic anhydride and 1,3-cyclohexadiene to give 3',4,7,7'-tetrahydro-4,7-ethaneisobenzofuran-1,3-dione is carried out at RT in dichloromethane as solvent. The solution rapidly becomes lemon-yellow, with the colouration becoming weaker in the course of the reaction. The following tables show the reaction conditions, weights and volumes of the starting materials and catalysts.

TABLE

Reaction conditions, starting material weights, volumes and conversions of the Diels-Alder reaction.

| Cat | Cat amount, mol % | Maleic anhydride, g (mmol), 1 eq. | 1,3-Cyclohexadiene, ml (mmol), 1.5 eq. | Time, min | Conversion %* |
|---|---|---|---|---|---|
| $BiCl_3$ | 5 | 0.84 (8.6) | 1.2 (12.6) | 20 | 97 |
| $(C_2F_5)BiCl_2$ | 1 | 0.74 (7.5) | 1.1 (11.5) | 30 | 97 |
| $(C_2F_5)_2BiCl$ | 1 | 0.42 (4.3) | 0.6 (6.3) | 30 | 89 |

*Conversion calculations based on $^1H$- and $^{13}C$-NMR spectroscopy measurements based on maleic anhydride.

The results confirm that $(C_2F_5)BiCl_2$ and $(C_2F_5)_2BiCl$ are significantly more active catalysts in the Diels-Alder reaction compared with $BiCl_3$.

Example 8

Cyanosilylation Catalysed by tris(pentafluoroethyl)bismuthane, $Bi(C_2F_5)_3$

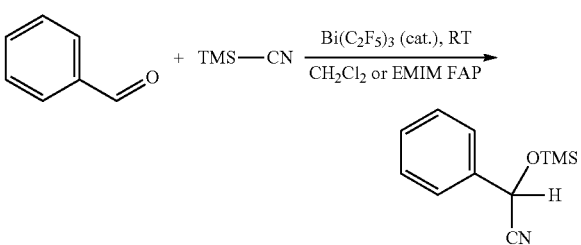

The cyanosilylation of benzaldehyde using trimethylsilyl cyanide to give 2-phenyl-2-(trimethylsilloxy)acetonitrile is carried out at room temperature in $CH_2Cl_2$ or 1-ethyl-3-methylimidazolium tris(pentafluoroethyl)trifluorophosphate (EMIM FAP) as solvent. The table below shows the reaction conditions, weights and volumes of the starting materials and catalysts.

TABLE

Reaction conditions, starting material weights, volumes and conversions of the cyanosilylation.

| Cat | Cat amount, mol %, (solvent) | Benzaldehyde, ml (mmol) | Trimethylsilyl cyanide, ml (mmol) | Time, h | Conversion, %* |
|---|---|---|---|---|---|
| $(C_2F_5)_3Bi$ | 5 ($CH_2Cl_2$) | 0.2 (2.0) | 0.4 (3.2) | 63 | 44 |
|  | 5 (EMIM FAP) | 0.2 (0.2) | 0.3 (2.4) | 19 | 66 |

*Conversion calculations based on $^1H$- and $^{13}C$-NMR spectroscopy measurements based on benzaldehyde.

The results show that, due to the good solubility of $(C_2F_5)_3Bi$ in the hydrophobic ionic liquid, the catalytic activity of $(C_2F_5)_3Bi$ in EMIM FAP is significantly increased compared with conventional organic solvents, such as $CH_2Cl_2$.

The invention claimed is:

1. A compound, which is of formula (I)

$$(C_mF_{2m+1})_nBiX_{3-n} \qquad (I),$$

wherein
m in each case, independently of one another, denotes 2, 3 or 4;
n denotes 1 or 2 and
X denotes F, Cl, Br or $OSO_2CF_3$,
or
which is of formula (IIIa) or (IIIb)

$$ArBi(C_mF_{2m+1})_2 \qquad (IIIa),$$

$$Ar_2Bi(C_mF_{2m+1}) \qquad (IIIb),$$

wherein
m in each case, independently of one another, denotes 2, 3 or 4 and
Ar in each case, independently of one another, denotes an aryl group having 6 to 10 C atoms, which may be substituted.

2. A compound according to claim 1, which is of formula (I)

$$(C_mF_{2m+1})_nBiX_{3-n} \qquad (I),$$

wherein
m in each case, independently of one another, denotes 2, 3 or 4;
n denotes 1 or 2 and
X denotes F, Cl, Br or $OSO_2CF_3$.

3. A compound according to claim 2, wherein m denotes 2 or 4.

4. A compound according to claim 2, wherein the compound of formula (I) is $Bi(C_2F_5)_2Cl$.

5. A compound according to claim 2, wherein the perfluoroalkyl group $(C_mF_{2m+1})$ in formula (I) is the same on each occurrence.

6. A compound according to claim 2, wherein X denotes Cl.

7. A process for preparing the compound of formula (I), $$(C_mF_{2m+1})_nBiX_{3-n} \qquad (I),$$

wherein
m in each case, independently of one another, denotes 2, 3 or 4;
n denotes 3 and
X denotes F, Cl, Br or $OSO_2CF_3$,
comprising reacting a compound of formula (II)

$$(C_mF_{2m+1})Li \qquad (II),$$

wherein
m denotes 2, 3 or 4,
with bismuth trichloride, bismuth tribromide or bismuth tristriflate,
where the conditions of the reaction are that both the water content and the oxygen content are a maximum of 100 ppm.

8. A process for preparing the compound of claim 2, comprising reacting a compound of formula (II)

$$(C_mF_{2m+1})Li \qquad (II),$$

wherein
m in each case, independently of one another, denotes 2, 3 or 4,
with dichloroarylbismuthane or chloro(diaryl)bismuthane, wherein aryl in the bismuthane denotes an aryl group having 6 to 10 C atoms, which may be substituted or unsubstituted, and the resultant intermediates of the formula (Ma) or (Mb)

$$ArBi(C_mF_{2m+1})_2 \qquad (IIIa) \text{ or}$$

$$Ar_2Bi(C_mF_{2m+1}) \qquad (IIIb),$$

are subsequently reacted with hydrogen chloride, hydrogen bromide, anhydrous HF or $CF_3SO_3H$ to give a compound of formula (I), wherein Ar in each case, independently of one another, denotes an aryl group having 6 to 10 C atoms, which may be substituted or unsubstituted, and where the conditions of the reaction with the compound of the formula (II) are that both the water content and the oxygen content are a maximum of 100 ppm.

9. A compound according to claim 1, which is of formula (IIIa) or (IIIb)

$$ArBi(C_mF_{2m+1})_2 \qquad (IIa),$$

$$Ar_2Bi(C_mF_{2m+1}) \qquad (IIIb),$$

wherein
m in each case, independently of one another, denotes 2, 3 or 4 and
Ar in each case, independently of one another, denotes an aryl group having 6 to 10 C atoms, which may be substituted.

10. A method for Lewis acid catalysis of a reaction, comprising performing said reaction in the presence of at least one compound according to claim 9 as the Lewis acid catalyst.

11. A compound according to claim 2, wherein n denotes 1.

12. A compound according to claim 2 The method, wherein n denotes 2.

13. A compound according to claim 2, wherein the compound of formula (I) is $Bi(C_2F_5)Cl_2$.

14. The compound according to claim 9, wherein the aryl group having 6 to 10 C atoms denotes phenyl or naphthyl, which may be mono- or polysubstituted by alkyl, fluorinated alkyl, Oalkyl or $N(alkyl)_2$.

15. The compound according to claim 9, wherein the aryl group having 6 to 10 C atoms denotes unsubstituted phenyl or naphthyl.

16. The process according to claim 8, wherein any of the aryl groups having 6 to 10 C atoms denotes phenyl or naphthyl, which may be mono- or polysubstituted by alkyl, fluorinated alkyl, Oalkyl or $N(alkyl)_2$.

17. The process according to claim 8, wherein any of the aryl groups having 6 to 10 C atoms denotes unsubstituted phenyl or naphthyl.

\* \* \* \* \*

UNITED STATES PATENT AND TRADEMARK OFFICE
CERTIFICATE OF CORRECTION

PATENT NO.        : 10,328,423 B2
APPLICATION NO.   : 15/762869
DATED             : June 25, 2019
INVENTOR(S)       : Berthold Theo Hoge et al.

Page 1 of 1

It is certified that error appears in the above-identified patent and that said Letters Patent is hereby corrected as shown below:

In the Claims

Column 16, Line 39 reads: "of the formula (Ma) or (Mb)" should read --of the formula (IIIa) or (IIIb)--.

Column 17, Lines 3 and 4 read: "A compound according to claim 2 The method, wherein n denotes 2." should read --A compound according to claim 2, wherein n denotes 2--.

Signed and Sealed this
Twelfth Day of November, 2019

Andrei Iancu
*Director of the United States Patent and Trademark Office*